US010550065B2

(12) United States Patent
Benstead et al.

(10) Patent No.: US 10,550,065 B2
(45) Date of Patent: Feb. 4, 2020

(54) WOOD ACETYLATION PROCESS

(71) Applicant: Tricoya Technologies Ltd, London (GB)

(72) Inventors: Stephen John Benstead, London (GB); Benjamin Thomas Painter, London (GB)

(73) Assignee: Tricoya Technologies Ltd, Windsor Berkshire (GB)

( * ) Notice: Subject to any disclaimer, the term of this patent is extended or adjusted under 35 U.S.C. 154(b) by 0 days.

(21) Appl. No.: 15/326,681

(22) PCT Filed: Jul. 17, 2015

(86) PCT No.: PCT/EP2015/066429
§ 371 (c)(1),
(2) Date: Jan. 17, 2017

(87) PCT Pub. No.: WO2016/009050
PCT Pub. Date: Jan. 21, 2016

(65) Prior Publication Data
US 2017/0204043 A1    Jul. 20, 2017

(30) Foreign Application Priority Data

Jul. 18, 2014  (GB) .................................. 1412839.1

(51) Int. Cl.
*C07C 51/56* (2006.01)
*B27K 3/34* (2006.01)
(Continued)

(52) U.S. Cl.
CPC ............ *C07C 51/56* (2013.01); *B27K 3/0292* (2013.01); *B27K 3/346* (2013.01); *C07C 51/44* (2013.01);
(Continued)

(58) Field of Classification Search
CPC ........ B27K 3/0292; B27K 3/346; B27K 3/02; B27K 3/10; B27K 3/0291; B27K 3/34;
(Continued)

(56) References Cited

U.S. PATENT DOCUMENTS 2,743,296 A     4/1956  Painter et al.
2004/0258941 A1* 12/2004 Neogi ....................... C08B 3/00
                                                      428/537.1
(Continued)

FOREIGN PATENT DOCUMENTS

EP        0213252       3/1987
EP        1 491 305    12/2004
WO       WO 99/59950    5/1999

OTHER PUBLICATIONS

Rowell, R. M., et al., Deterioration and Protection of Sustainable Biomaterials, Acetylation of Wood, Chapter 18, 2014 American Chemical Society Symposium Series, vol. 1158, pp. 301-327, (Year: 2014).*

(Continued)

*Primary Examiner* — Yate' K Cutliff
(74) *Attorney, Agent, or Firm* — OspreyIP, pllc; James R. Cartiglia

(57) ABSTRACT

Disclosed is the integration of the production of acetic anhydride from ketene, and the acetylation of wood using acetylation fluid comprising acetic acid and acetic anhydride. The invention involves directly using raw acetic anhydride as obtained in the production thereof from ketene, as a wood acetylation fluid.

6 Claims, 2 Drawing Sheets

(51) Int. Cl.
*B27K 3/02* (2006.01)
*C08B 3/06* (2006.01)
*C07C 51/44* (2006.01)
*C08H 8/00* (2010.01)
*B27K 3/36* (2006.01)
*B05D 7/06* (2006.01)
*B27K 3/10* (2006.01)

(52) U.S. Cl.
CPC ............... *C08B 3/06* (2013.01); *C08H 8/00* (2013.01); *B05D 7/06* (2013.01); *B27K 3/02* (2013.01); *B27K 3/10* (2013.01); *B27K 3/34* (2013.01); *B27K 3/36* (2013.01)

(58) Field of Classification Search
CPC ........... B27K 3/36; C07C 51/44; C07C 51/56; C07C 49/90; C08B 3/06; C08B 3/20; C08H 8/00; Y02P 20/125; B05D 7/06
See application file for complete search history.

(56) References Cited

U.S. PATENT DOCUMENTS

2009/0234157 A1    9/2009  Warner et al.
2013/0197267 A1*  8/2013  Warner .................. C07C 51/56
                                      562/890

OTHER PUBLICATIONS

Callum A.S. Hill, Wood Modification: Chemical, thermal and Other Processes, 2006 John Wiley & Sons, Ltd.
Rowell and Dickerson, Acetylation of Wood, 2014 American Chemical Society Symposium Series.

* cited by examiner

WOOD ACETYLATION PROCESS

FIELD OF THE INVENTION

The invention pertains to a process wherein the production of acetic anhydride from acetic acid is coupled to a process for the acetylation of wood. Also, the invention relates to an integrated system for the purification of acetic anhydride and the acetylation of wood.

BACKGROUND OF THE INVENTION

A well-known process for the production of acetic anhydride from acetic acid involves the formation of ketene (ethenone). Thereby ketene is produced by dehydrating acetic acid at high temperatures (typically in a ketene furnace operated at temperatures of the order of 700° C. to 750° C.). Subsequently, the ketene is reacted with acetic acid in an exothermic reaction leading to the formation of acetic anhydride.

Interestingly, both acetic acid and acetic anhydride are used in processes for the acetylation of wood. These processes, for which there is an increasing demand, serve to provide the wood with improved material properties, e.g. dimensional stability, hardness, durability, etc. In these processes, excess acetylation medium, typically a mixture of acetic anhydride and acetic acid, is ultimately removed from the wood. It is thereby desired to avoid wasting the removed acetylation medium, and preferably to recirculate and re-use it in wood acetylation.

It is desired to provide a method by which the acetylation of wood and the production of acetic anhydride can be effectively integrated, preferably with reduced equipment and operational expenses. Also, it is desired to thereby make optimal use of sources of liquid as available from wood acetylation.

SUMMARY OF THE INVENTION

In order to better address one or more of the foregoing desires, the invention, in one aspect, concerns a process for the acetylation of wood, wherein the wood acetylation process is coupled to a process for the production of acetic anhydride, the wood acetylation process comprising subjecting wood to acetylation using an acetylation fluid, and the acetic anhydride production process comprising reacting ketene with acetic acid so as to form a raw anhydride reaction fluid comprising acetic anhydride and acetic acid, wherein the raw anhydride reaction fluid is used as an acetylation fluid in the wood acetylation process.

In another aspect the invention presents a system comprising a wood acetylation plant and an acetic anhydride production plant, wherein the wood acetylation plant comprises a wood acetylation unit comprising an inlet and an outlet for acetylation fluid, and wherein the acetic anhydride production plant comprises a unit for the production of acetic anhydride from ketene and acetic acid and wherein an outlet for a product stream from the unit for the production of acetic anhydride is in direct fluid communication with an inlet for acetylation fluid in the wood acetylation unit.

DETAILED DESCRIPTION OF THE INVENTION

Figure 1:
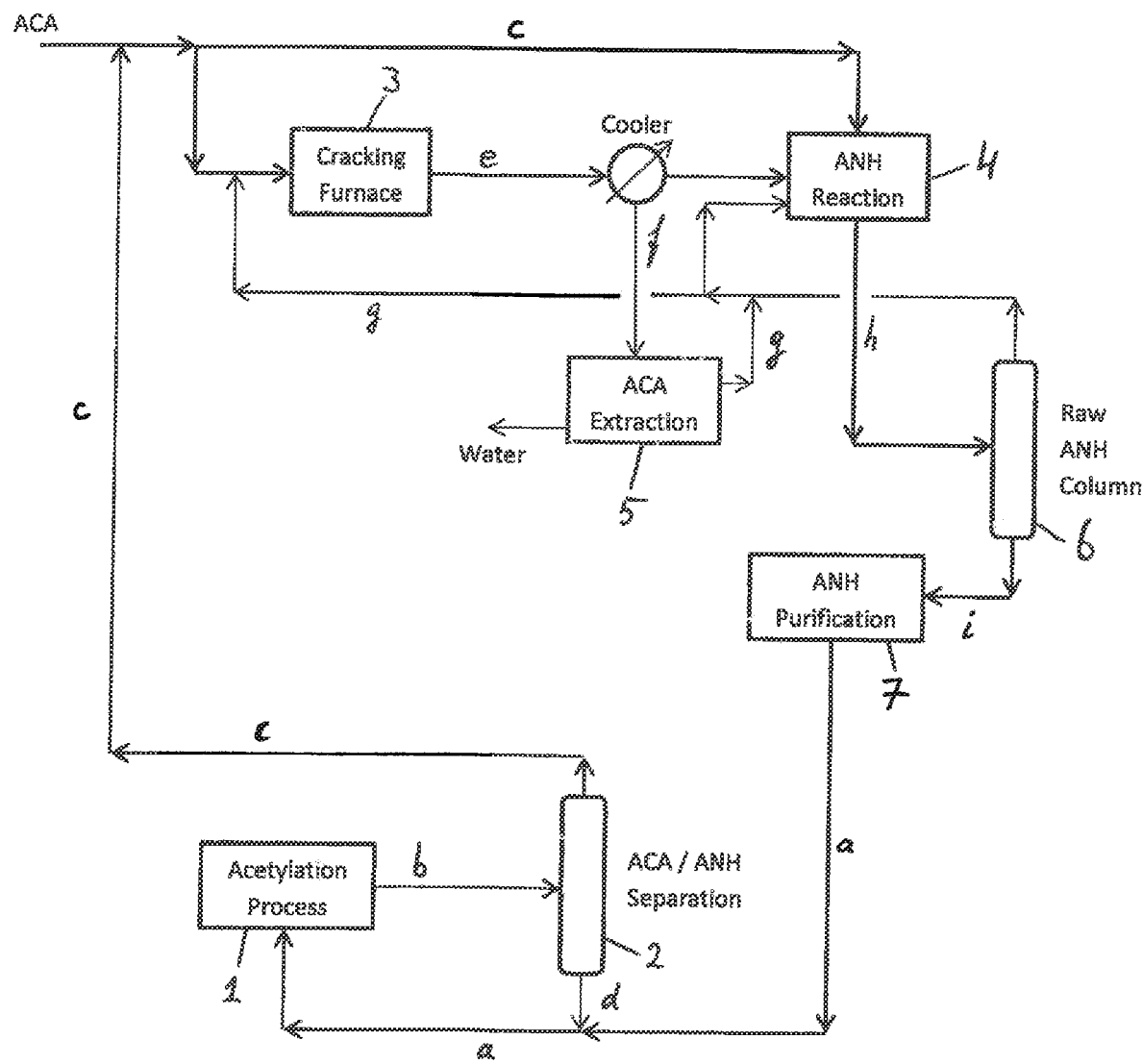
FIG. 1 shows a scheme for a wood acetylation plant coupled to an acetic anhydride production plant without additional measures, not according to the invention.

In a broad sense, the invention is based on the judicious insight to directly use fluid obtained from anhydride production, without distilling off acetic acid, in wood acetylation. By doing so, the normally present distillation equipment downstream of the reaction zone in which acetic anhydride is produced from ketene and acetic acid, can be dispensed with.

In the process of the invention, acetylation fluid recovered from wood acetylation is preferably used, in turn, in the production of acetic anhydride. This can be done by subjecting recovered acetylation fluid to acetic acid from acetic anhydride separation (typically by distillation), and using the acetic acid thereby obtained as a reactant in the production of acetic anhydride. The latter can be either in the production of ketene from acetic acid, or in the production of acetic anhydride from acetic acid and ketene, or it can be used in both. Thus, a recirculation loop is provided wherein both the acetylation of wood and the production of acetic anhydride from ketene are comprised, and acetylation fluid is re-used to the extent possible. The anhydride recovered from the acetic acid/acetic anhydride separation, can be recirculated as well, and re-used in the wood acetylation fluid.

In a preferred embodiment, the process of the invention is adjusted so as to improve the suitability of the recovered acetic acid in the production of ketene. This relates to the fact that the acetic acid obtained from recovered wood acetylation fluid, may comprise impurities drawn from wood, such as terpenes and terpenoids. Particularly terpenes and terpenoids are difficult to remove, but it would be preferred to avoid these from being used in the production of ketene. Using acetic acid as recovered from wood acetylation in a ketene furnace, brings about a risk that the aforementioned impurities are prone to result in coke formation in the furnace, due to the high temperatures applied therein.

In one preferred embodiment, the acetic acid obtained from the recovered acetylation fluid is therefore used in the second step of the production of acetic anhydride, viz., in the reaction between acetic acid and ketene. In another preferred embodiment, the acetic acid obtained from the recovered wood acetylation fluid is mixed with a residual aqueous acetic acid stream from ketene production. When this aqueous stream is subjected to acetic acid extraction (by distillation), terpene and terpenoid impurities are allowed to be removed by forming an azeotrope with water. This azeotropic removal of terpenes in itself is known, see WO 2009/120257.

The integration of wood acetylation and acetic anhydride production according to the invention can be carried out both in existing plants and in designing new plants. E.g., a new ketene-based production unit for acetic anhydride can be built next to an existing wood acetylation unit, and coupled to it in accordance with one or more embodiments of the invention. Also, a new wood acetylation unit can be built next to an existing ketene-based production unit for acetic anhydride. Or, in the event that a wood acetylation unit and a ketene-based acetic anhydride production unit already exist next to each other, these can become integrated. In the event that the units are already integrated in another way, the manner in which such plants are coupled can be changed so as to be in conformity with the invention as described hereinbefore.

The equipments and technologies applied are well-known to the skilled person. This pertains to units for the acetylation of wood, such as wood acetylation reactors, and the customary ancillary equipment thereof, e.g. a filter section for removing wood residues from recovered acetylation fluid. Similarly, this pertains to distillation units (distillation equipment such as a distillation column), to ketene production sections (typically a ketene furnace), acetic anhydride production sections (typically a reactor suitable for reacting ketene with acetic acid).

Wood acetylation units for use in the present invention can be those suitable for the acetylation of solid wood, such as wood beams or planks Said wood acetylation units can also be those suitable for the acetylation of wood elements such as flour, fibres, strands, or chips. The wood acetylation processes applied in the present invention thus are not limited to any size, shape, or species of wood. A great variety of such processes is well-known to the skilled person.

The invention also pertains to the integration of a wood acetylation plant and an acetic anhydride production plant. In this aspect, the invention provides a system comprising a wood acetylation plant and an acetic anhydride production plant. The wood acetylation plant comprises a wood acetylation unit comprising an inlet and an outlet for acetylation fluid. The acetic anhydride production plant comprises a unit for the production of acetic anhydride from ketene and acetic acid. The latter unit comprises an outlet for a product stream, which is in untreated direct fluid communication with an inlet for acetylation fluid in the wood acetylation unit. The term "direct" herein does not mean that said fluid communication necessarily is through a single duct or flow line. Also, any duct or other means of fluid transportation from the outlet of the acetic anhydride production plant to the inlet of the wood acetylation unit, can comprise bends, reservoirs, valves, and the like. The term "direct" serves to indicate that the fluid transported does not pass a section where it is treated in such a way that its composition is substantially changed, such as would be the case in the event of distillation as would conventionally occur.

In an interesting embodiment, the system of the invention is further arranged so as to make it possible for acetic acid, separated from recovered acetylation fluid, to be sent to a treatment section belonging to the production of ketene in the acetic anhydride production plant, in which residual aqueous acetic acid is subjected to distillation. To this end, the system of the invention comprises, downstream of the acetylation unit, a unit for the separation of acetic acid from acetic anhydride, such as a distillation column, which unit has an outlet for distillate that is in fluid communication with an inlet of said treatment section for residual aqueous acetic acid.

The foregoing embodiment can be of particular advantage in wood acetylation plants that already contain a distillation unit for recovered acetylation fluid. In that event, the integration of such an existing wood acetylation unit with a ketene-based acetic anhydride production unit can be advantageously carried out by arranging the appropriate flow lines so as to have acetic acid retrieved in said distillation unit combined with the residual aqueous acetic acid stream from ketene production.

The invention will be further explained hereinafter with reference to the drawings. These drawings do not limit the invention. As the drawings may relate to specific embodiments of the invention, the skilled person will understand that the invention is more generally applicable, and the disclosure in the drawings is not limited to any specific designs or numbers given therein.

In the figures, the following elements are shown.

Equipment parts:
(1) Wood acetylation plant
(2) Acetic acid/acetic anhydride separation unit
(3) Ketene production unit
(4) Acetic anhydride production unit
(5) Treatment section for recovering residual aqueous acetic acid
(6) Acetic anhydride distillation unit
(7) Acetic anhydride purification unit Process streams:
(a) Fresh acetylation fluid
(b) Acetylation fluid recovered from wood acetylation
(c) Acetic acid
(d) Acetic anhydride separated from acetic acid
(e) Ketene
(f) Residual aqueous acetic acid
(g) Acetic acid recovered
(h) Raw acetic anhydride (mixture with acetic acid)
(i) Enriched acetic anhydride (reduced acetic acid content)

FIG. 1 shows a scheme for a ketene-based acetic anhydride production plant (comprising a ketene production unit (3) and an acetic anhydride production unit (4) integrated with a wood acetylation plant (1). Herein the plants are coupled without any additional measures, i.e. not according to the invention. Acetylation fluid (stream a) is fed to a wood acetylation plant (1). Recovered acetylation fluid (b) is subjected to acetic acid separation in a first acetic acid/acetic anhydride separation unit (2), resulting in a stream (c) of acetic acid separated from acetic anhydride and a stream (d) of acetic anhydride separated from acetic acid. The stream (c) of acetic acid separated from acetic anhydride is sent to an acetic anhydride production section comprising a ketene production unit (3) and an acetic anhydride production unit (4). The ketene production unit (3) is connected to, downstream thereof, a treatment section (5) for recovering residual aqueous acetic acid (f). Acetic acid recovered therefrom (g) is sent to the ketene production unit (3) and/or the acetic anhydride production unit (4). Ketene produced (e) is sent to an acetic anhydride production unit (4). Raw anhydride produced (h) is sent to an acetic anhydride distillation unit (6). Acetic acid obtained therefrom (c) is sent to the acetic anhydride production section mentioned above. The enriched acetic anhydride (i), having a reduced acetic acid content, is sent to a purification unit (7) and purified acetylation fluid thereby obtained (i) is fed, as fresh acetylation fluid (a) to the wood acetylation section (1).

Figure 2:
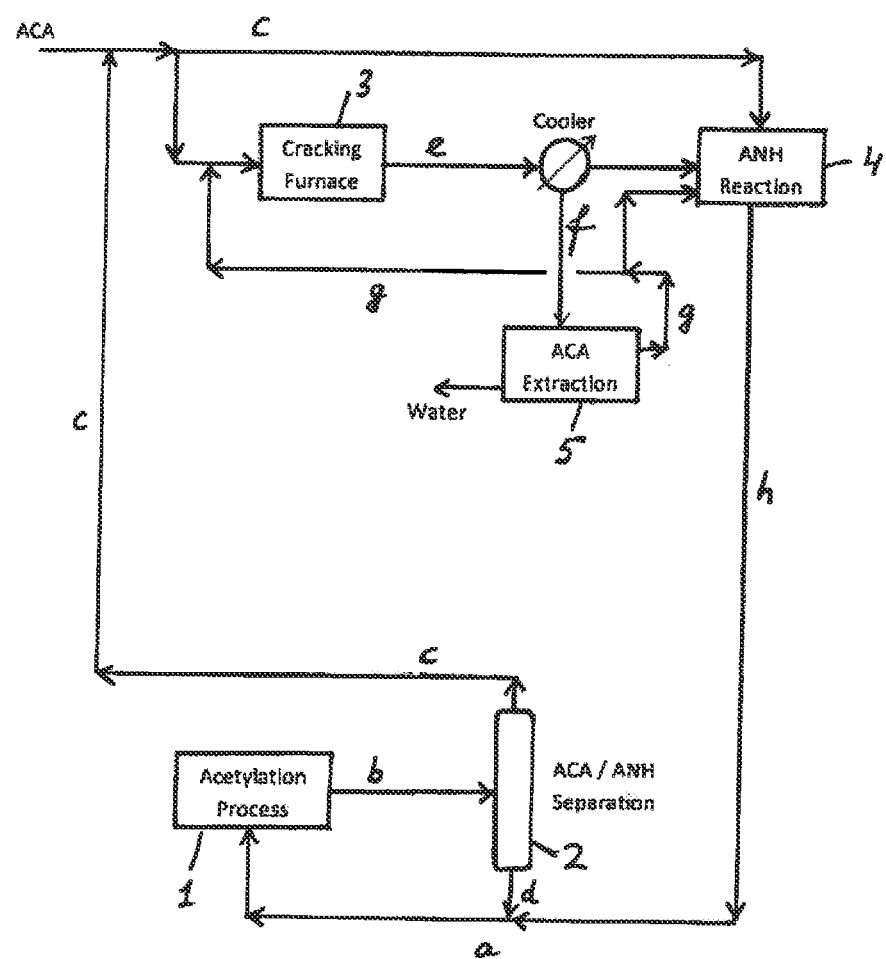
FIG. 2 shows a scheme for a wood acetylation plant coupled to an acetic anhydride production plant according to an embodiment of the invention.

FIG. 2 shows a scheme for a ketene-based production plant for acetic anhydride integrated with a wood acetylation plant, comprising a wood acetylation unit (1), in accordance with an embodiment of the invention. Herein the stream of produced acetic anhydride, with acetic acid (h) is sent, as an acetylation fluid stream (a) to the wood acetylation unit (1).

It will be understood that the schematic drawings serve to illustrate some parts of the equipments and production units as necessary to further illustrate some embodiments of the invention. The skilled person will be well aware of equipment parts and flow lines now shown, such as devices for providing heat, devices for providing pressure, vents for off-gas, and so on.

Where, in this description, it is spoken of "fluid communication", this refers to any connection between a first part or section of a plant and a second part or section of a plant via which fluids, including liquids and gases, can flow from the first part of the plant to the second part of the plant. In the event of liquids, such fluid communication is typically provided by piping systems, hoses, or other devices well-known to the skilled person for the transportation of fluids. In the event of gases, such fluid communication is typically provided by gas flow lines. Such gas flow lines typically comprise piping systems, or other devices well-known to the skilled person for the transportation of gases, if needed under pressures that are above atmospheric pressures or below (vacuum).

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein described units, such as a wood acetylation unit, a reactor unit or a distillation unit, comprise a plurality of such units positioned in parallel or in series.

Other variations to the disclosed embodiments can be understood and effected by those skilled in the art in practicing the claimed invention, from a study of the drawings, the disclosure, and the appended claims In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

The invention claimed is:

1. A process for the acetylation of wood, wherein the wood acetylation process is coupled to a process for the production of acetic anhydride, the wood acetylation process comprising subjecting wood to acetylation using an acetylation fluid, and the acetic anhydride production process comprising reacting ketene with acetic acid so as to form a raw anhydride reaction fluid comprising acetic anhydride and acetic acid, wherein the raw anhydride reaction fluid is used in the wood acetylation process as an acetylation fluid without distilling off acetic acid from the raw anhydride reaction fluid formed by the step of reacting ketene with acetic acid.

2. A process according to claim 1, wherein the ketene is produced in a ketene production process comprising heating acetic acid under ketene forming conditions, and using the produced ketene as a reactant in the acetic anhydride production process.

3. A process according to claim 1 or 2, comprising recovering wood acetylation fluid from the wood acetylation process to obtain recovered acetylation fluid comprising acetic acid and acetic anhydride, and subjecting the recovered acetylation fluid to distillation so as to obtain acetic acid, wherein said acetic acid is used as a reactant in either or both of the acetic anhydride production process and the ketene production process.

4. A process according to claim 3, wherein the obtained acetic acid, prior to being used as a reactant, is purified by mixing it with an aqueous waste stream from the ketene production process, and subjecting the resulting mixture to distillation.

5. A process according to claim 4, wherein all of the purified acetic acid is used as a reactant in the ketene production process.

6. A system comprising a wood acetylation plant and an acetic anhydride production plant, wherein the wood acetylation plant comprises a wood acetylation unit comprising an inlet and an outlet for acetylation fluid, and wherein the acetic anhydride production plant comprises a unit for the production of acetic anhydride from ketene and acetic acid and wherein an outlet for a product stream from the unit for the production of acetic anhydride is in direct fluid communication with the inlet for acetylation fluid in the wood acetylation plant without distilling off acetic acid in the wood acetylation unit.

* * * * *